United States Patent
Huang et al.

(10) Patent No.: US 8,016,986 B2
(45) Date of Patent: Sep. 13, 2011

(54) ELECTROCHEMICAL SENSING TEST PIECE WITHOUT HEMOCYTE INTERFERENCE

(75) Inventors: Tong-Yuh Huang, Jhubei (TW);
Chin-Chia Lin, Lujhu Township, Taoyuan County (TW); Hui-Fang Wang, Hukou Township, Hsinchu County (TW)

(73) Assignee: Sand County Biotechnology, Inc., Hu-Ko, Hsin-Chu County (TW)

( * ) Notice: Subject to any disclaimer, the term of this patent is extended or adjusted under 35 U.S.C. 154(b) by 309 days.

(21) Appl. No.: 12/410,689

(22) Filed: Mar. 25, 2009

(65) Prior Publication Data
US 2010/0243442 A1    Sep. 30, 2010

(51) Int. Cl.
*G01N 27/327* (2006.01)
(52) U.S. Cl. ............... 204/403.06; 204/403.05
(58) Field of Classification Search .......... 204/403.01–403.15; 205/77.5, 205/778, 792
See application file for complete search history.

(56) References Cited

U.S. PATENT DOCUMENTS

| | | | | |
|---|---|---|---|---|
| 6,565,808 | B2 * | 5/2003 | Hudak et al. | 422/411 |
| 7,198,708 | B2 * | 4/2007 | Atkinson et al. | 205/787 |
| 2004/0231983 | A1 * | 11/2004 | Shen et al. | 204/403.01 |
| 2005/0072670 | A1 * | 4/2005 | Hasegawa et al. | 204/403.01 |

* cited by examiner

*Primary Examiner* — Alex Nouguerola
(74) *Attorney, Agent, or Firm* — Egbert Law Offices PLLC

(57) ABSTRACT

The present invention provides an electrochemical sensing test piece without hemocyte interference, including a main body, electrode unit, reaction tank and chemical reaction zone. The detection zone of the electrode unit corresponds to the inserting end of the main body, and the reaction zone of the electrode unit corresponds to the sensing end of the main body. The reaction tank is arranged onto the sensing end correspondingly to the reaction zone of the electrode unit. The reaction tank is provided with a porous filter layer, whose aperture must be less than 6 μm for or separation of hemocyte in the blood sample. A chemical reaction zone is arranged between the porous filter layer and the reaction zone of the electrode unit. The hemocyte of the blood sample can be blocked and filtered by the porous filter layer, ensuring that the serum of blood sample can enter into the chemical reaction zone.

7 Claims, 9 Drawing Sheets

ELECTROCHEMICAL SENSING TEST PIECE WITHOUT HEMOCYTE INTERFERENCE

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates generally to an electrochemical sensing test piece, and more particularly to an innovative testing piece with a porous filter layer mounted on a reaction tank.

2. Description of Related Art Including Information Disclosed Under 37 CFR 1.97 and 37 CFR 1.98

Currently, a blood-glucose meter detects chemical levels based on optical and electrochemical principles. Using the optical principle, color of a reagent paper changes after reaction between glucose in blood and fermentation in the reagent paper. Then, reflected rays are detected by an optical lens, creating signals that turn into a blood glucose value. Using the electrochemical principle, there is a particular and controlled chemical reaction of blood glucose to produce electrons on a sensing test piece. The electrons generated accumulate on an electrode surface of the sensing test piece, then, a fixed voltage is provided to detect the number of electrons and current on the electrode surface. Using a conversion formula embedded into the blood glucose tester, users can calculate the concentration of glucose in the blood.

However, the portable prior art device integrating the blood glucose tester and sensing test piece often make a large amount of measurement error, primarily because of the hematocrit (HCT) in the blood sample. The different effects generated by HCT include: 1) varying blood concentrations, which leads to inconsistent electronic transmission efficiency, thus affecting the final measurement; and 2) causing inconsistent volumes of serum, requiring different and changing measurement criteria.

Furthermore, the sensing test piece is structured in such a manner that a slotted groove is placed laterally onto the sensing end, enabling the user to drip a little blood sample into the groove. Then, the blood sample absorbs into this groove by siphoning, so as to generate a chemical reaction with the internally-set electrochemical reaction unit. Because of the inconsistent concentrations of serum and hemocyte in the blood of users (including: human beings and animals) when the users drip the blood sample into the groove, the sample volume of blood serum absorbed every time into the groove and fed to the electrochemical reaction unit for reaction will vary from different interferences arising from hemocyte concentrations. The different degrees of blood concentration will certainly cause variations in each reaction and inaccuracy of measurement.

The currently available electrochemical sensors based on oxidases are vulnerable to the influence of oxygen content in the samples. Conversely, it is observed that some dehydrogenase sensors are affected by other in-vivo drugs or metabolites, leading to abnormal measurements. For instance, the measurement accuracy will be lost due to the influence of drug metabolites, when peritoneal dialysis is used for the blood glucose of nephrotics.

Thus, to overcome the aforementioned problems of the prior art, it would be an advancement in the art to provide an improved structure that can significantly improve efficacy.

Therefore, the inventor has provided the present invention of practicability after deliberate design and evaluation based on years of experience in the production, development and design of related products.

BRIEF SUMMARY OF THE INVENTION

Based on the unique present invention, there is a porous filter layer having an aperture less than 6 μm arranged in a reaction tank. A chemical reaction zone is arranged between the porous filter layer and electrode unit reaction zone. The electrochemical sensing test piece of the present invention, as compared with the prior art, enables the hemocyte of the blood sample to be blocked and filtered by the porous filter layer. Also, it ensures that the serum of blood sample can enter into the chemical reaction zone, allowing the electrochemical sensing test piece to remove the interference factors such as HCT and oxygen content, thereby greatly improving the sensing accuracy and adjusting for the diversification of test samples.

Based on the structure of the present invention, a quantitative diversion layer is arranged between the porous filter layer and the chemical reaction zone. The blood sample flowing through the porous filter layer can be restricted to ensure consistent quantity of blood sample and improve the sensing accuracy and quality.

Based on the present invention, the porous filter layer contains protein absorbent to absorb the protein content in the blood sample so as to obtain purified serum. Since the blood concentration in the serum is also affected by the protein content, the porous filter layer of the present invention is provided additionally with protein absorbent to further purify the separated serum sample and provide more accurate measurement results.

While it is intended to remove interference factors in the blood, a consistent and accurate measurement can be made possible for the human blood and animal blood samples of various contents.

Although the invention has been explained in relation to its preferred embodiment, it is to be understood that many other possible modifications and variations can be made without departing from the spirit and scope of the invention as hereinafter claimed.

DETAILED DESCRIPTION OF THE INVENTION

Figure 1:
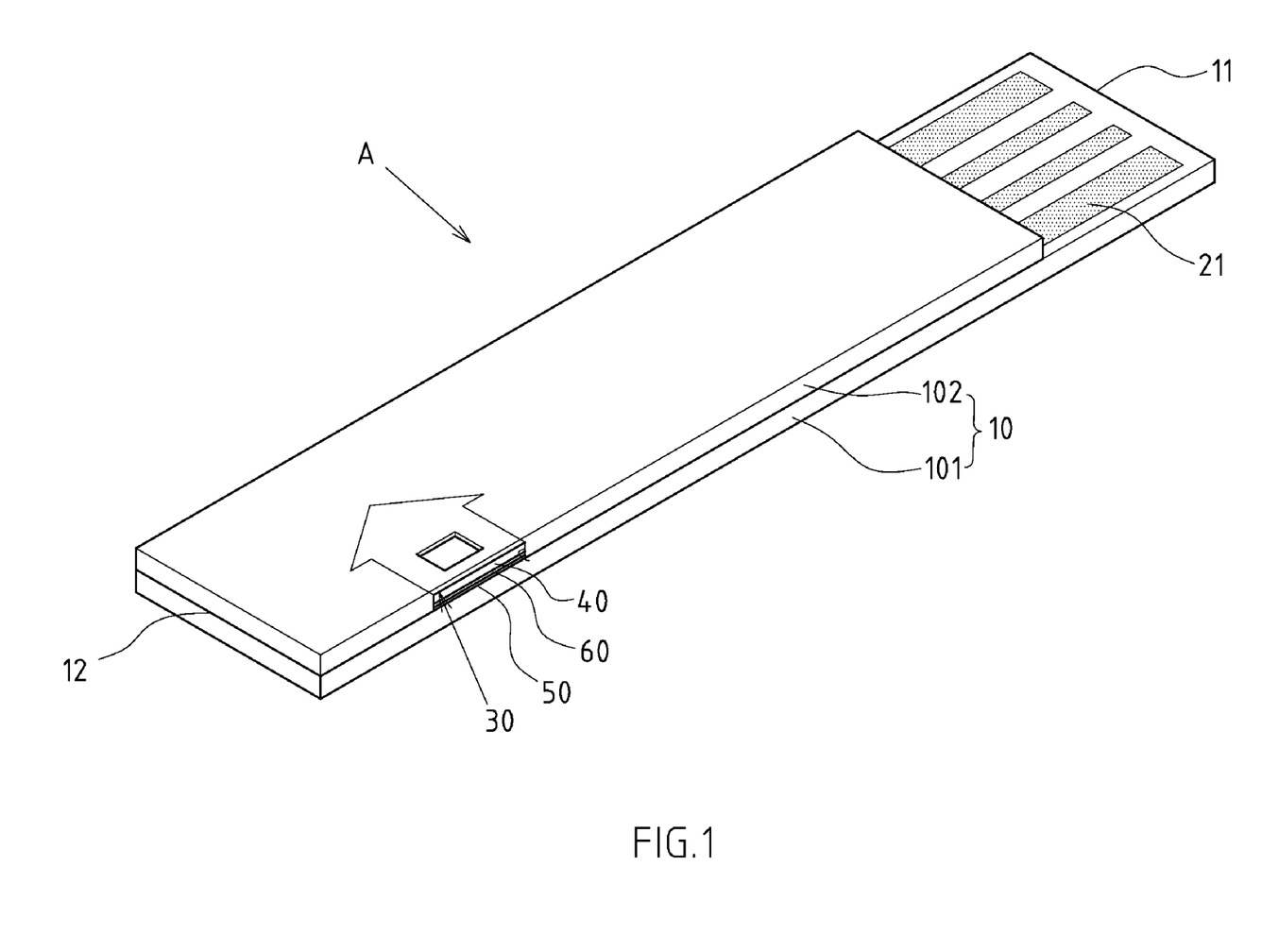
FIG. 1 shows an assembled perspective view of the preferred embodiment of the electrochemical sensing test piece of the present invention.
Figure 2:
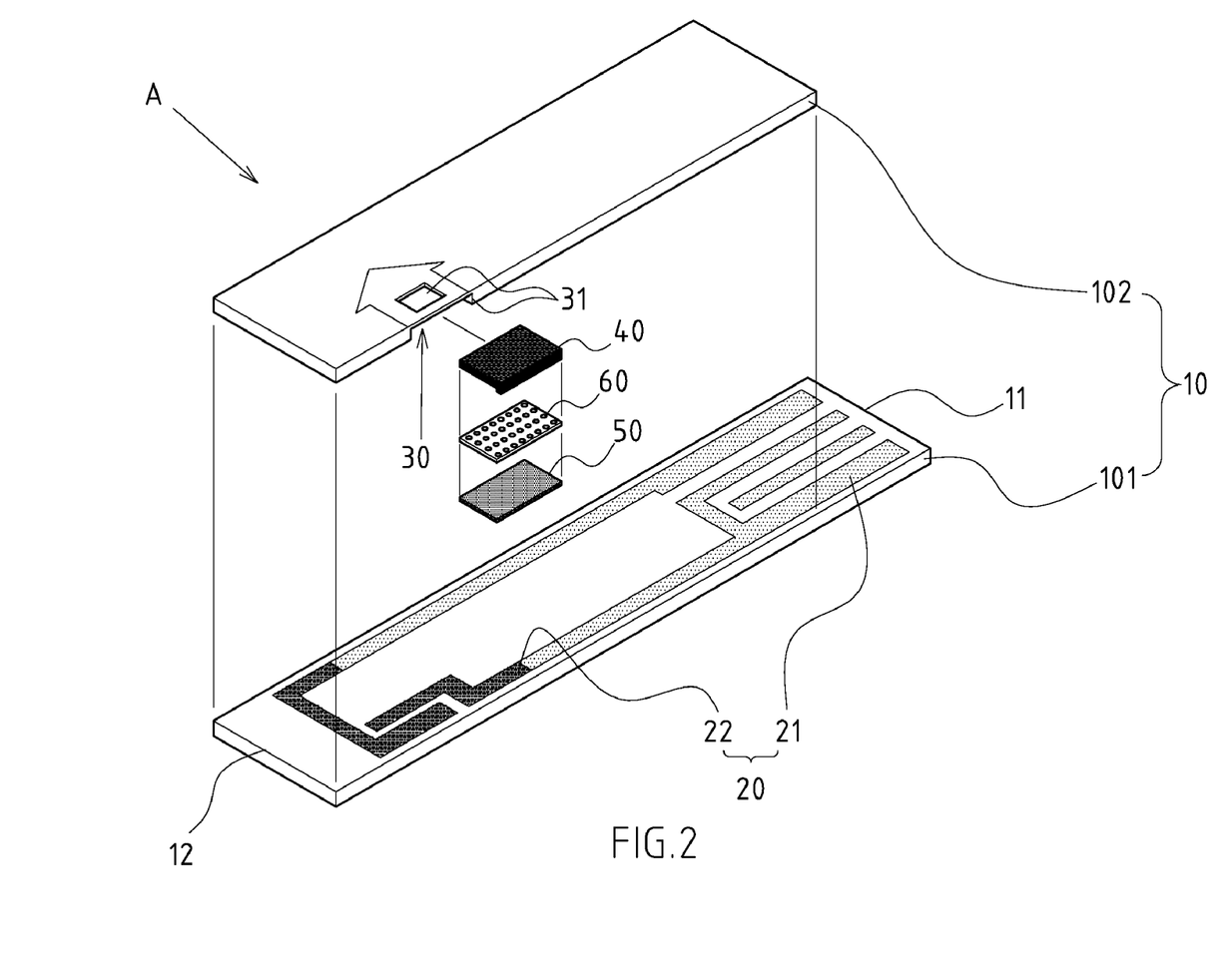
FIG. 2 shows an exploded perspective view of the preferred embodiment of the electrochemical sensing test piece of the present invention.

FIGS. 1-2 depict preferred embodiments of electrochemical sensing test piece of the present invention without hemocyte interference. The embodiments are only provided for explanatory purposes with respect to the patent claims.

The electrochemical sensing test piece A includes a main body 10, which is a long sheet. The main body 10 contains an inserting end 11 and a sensing end 12. The main body 10 is superimposed by an insulating substrate 101 (e.g. plastic sheet) and a cover plate 102.

An electrode unit 20 is arranged laterally onto the insulating substrate 101 of the main body 10. The electrode unit 20 contains a detection zone 21 and a reaction zone 22. The detection zone 21 corresponds to the inserting end 11 of the main body 10, and the reaction zone 22 corresponds to the sensing end 12 of the main body 10.

A reaction tank 30 is arranged onto the sensing end 12 of the main body 10 corresponding to the reaction zone 22 of the electrode unit 20. Moreover, the reaction tank 30 is provided with a test sample port 31 for the blood sample. The test sample port 31 can be opened on the side or on the top.

A porous filter layer 40 is placed into the reaction tank 30. The porous filter layer 40 is of a porous structure, and the aperture must be less than 6 µm for separation of over 6 µm hemocyte in the blood of human beings and animals. This pore passes serum in the blood, while blocking off and filtering the hemocyte. Moreover, one side of the porous filter layer 40 can be extended to the test sample port 31 of the reaction tank 30.

A chemical reaction zone 50 is arranged between the porous filter layer 40 and the reaction zone 22 of the electrode unit 20, so that the serum filtered by the porous filter layer 40 can reach the chemical reaction zone 50. The chemical reaction zone 50 is made of a ferment, which can generate chemical reactions with the glucose in the sensing sample (e.g. blood sample), so that electrons are accumulated at the reaction zone 22 of the electrode unit 20. When the electrode unit 20 is energized with a fixed voltage, the number of electrons accumulated at the reaction zone 22 can be detected.

The porous filter layer 40 is made of flaky charcoal of a porous structure for filtering purpose. Besides, the porous filter layer 40 can also be made of the following materials:

Porous hydroxyapatite powder (HAp);

Attapulgiteclay or Montomorillonite, which is crushed and filtered, then centrifuged by a high-speed stirrer according to a water/soil percentage; next, the clay is dried, crushed and filtered to obtain a porous body;

Water gel;

Polymers, which are dissolved in a kind of solvent, then halogen is added; after volatilization of solvent, it is soaked in water and desalted to form a porous structure; and A 3D material, which is formed by 3D coating, and trichloromethane is added as an adhesive, then removed to obtain a porous structure.

A quantitative diversion layer 60 is additionally arranged between the porous filter layer 40 and the chemical reaction zone 50, so that the blood sample flowing through the porous filter layer 40 can be restricted to ensure consistent quantity of blood sample.

The hemocyte content in the blood sample treated by the porous filter layer 40 has been removed, so the measurement result is not affected by HCT in the blood. In addition, since the oxygen in the blood is mainly carried by heme on the erythrocyte, and the erythrocyte's test sample is removed by the porous filter layer 40, the measurement result isn't affected by the oxygen content in the blood, either. The blood samples of different oxygen contents, such as arterial blood, venous blood and capillary blood, can be measured consistently and accurately on the electrochemical sensing test piece A of the present invention.

Moreover, the porous filter layer 40 contains protein absorbent to absorb the protein in the blood sample and acquire purified serum. Since the blood concentration in the serum is also affected by the protein content, the porous filter layer 40 of the present invention is provided additionally with protein absorbent to further purify the separated serum sample.

Figure 3:
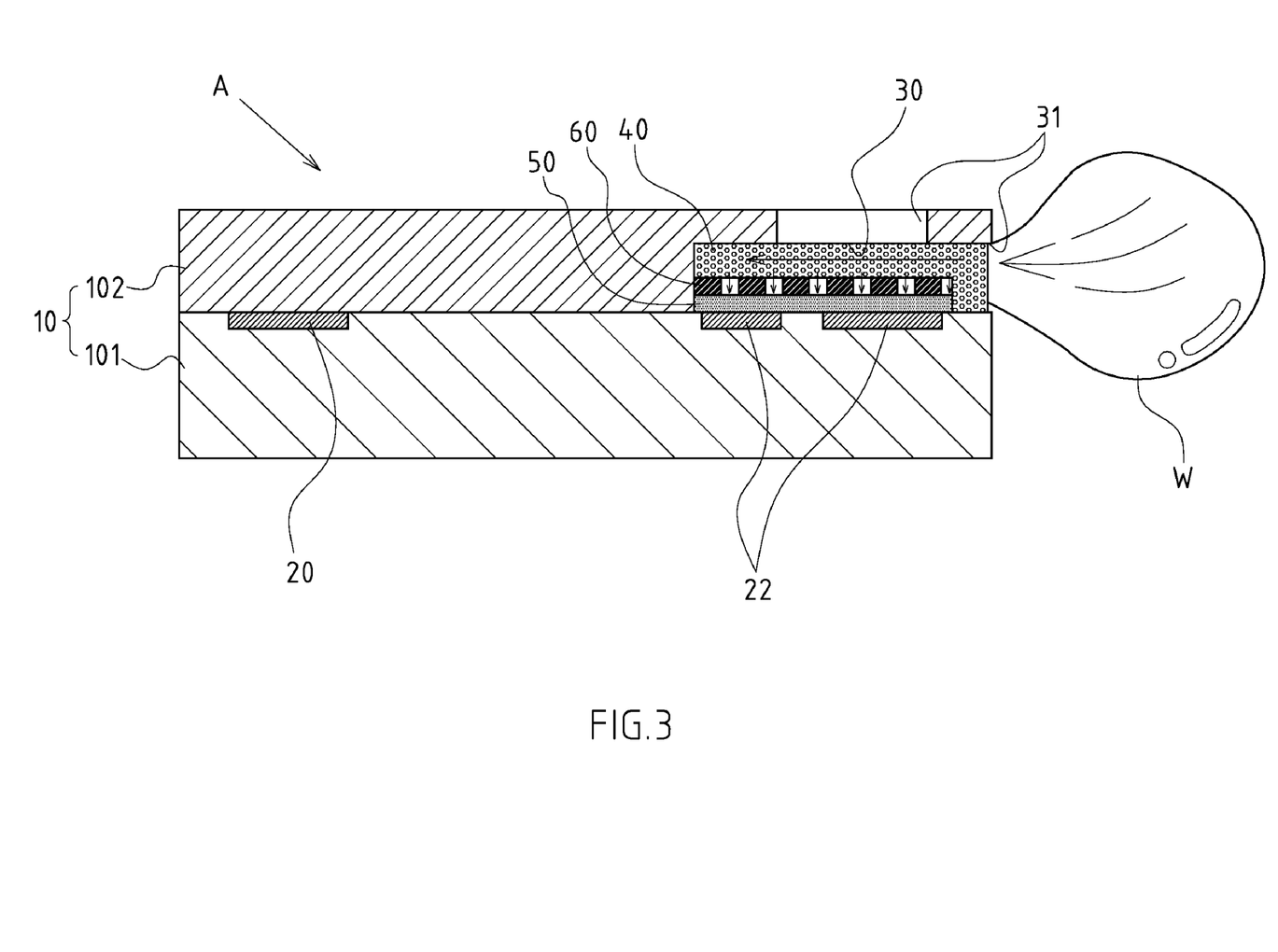
FIG. 3 shows a partially sectional view of the preferred embodiment of the electrochemical sensing test piece of the present invention.
Figure 4:
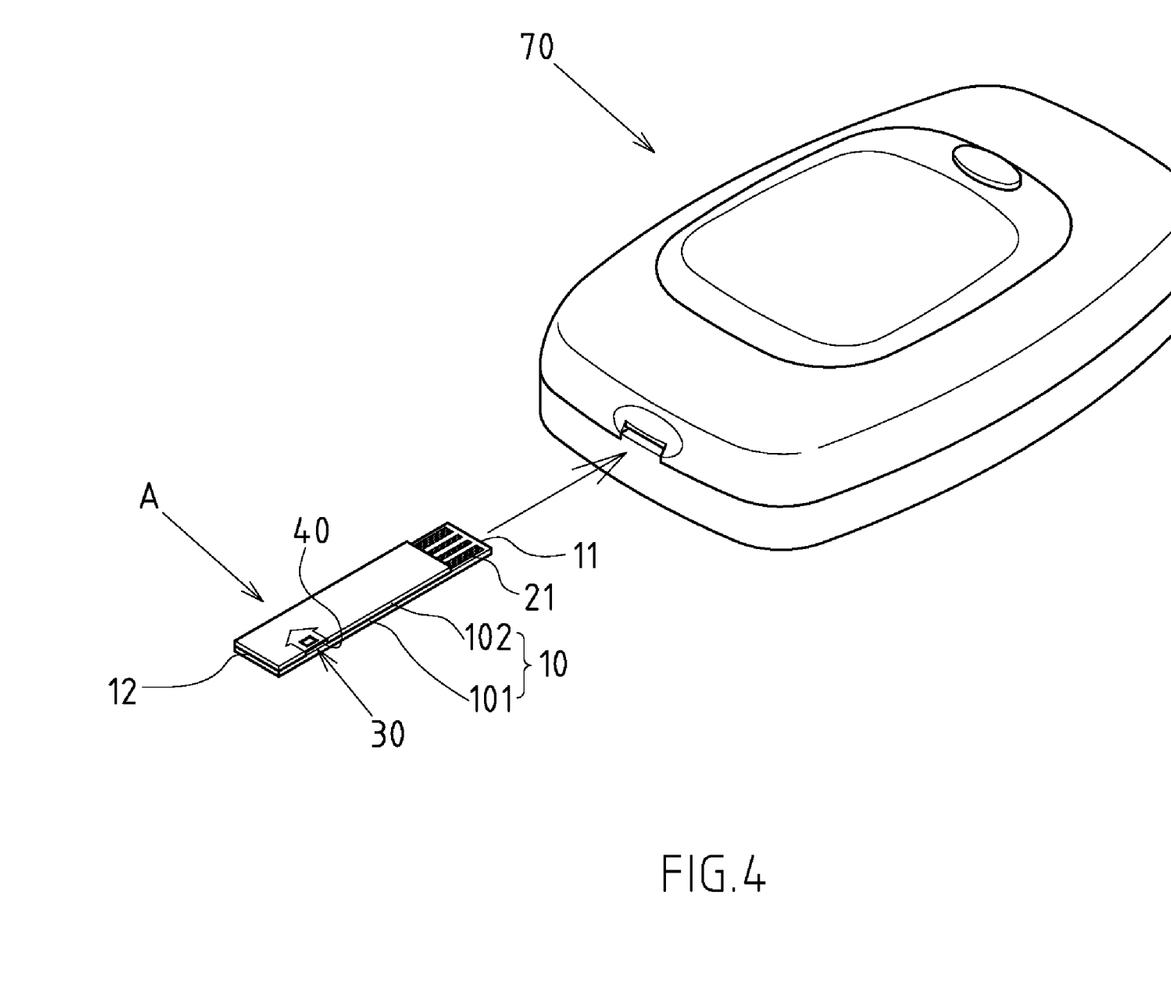
FIG. 4 shows a perspective view of an application of the present invention, showing the electrochemical sensing test piece combined with a blood glucose tester.

Based on the above-specified structures, the electrochemical sensing test piece A of the present invention is operated as shown in FIG. 4, wherein a blood glucose tester 70 is employed to measure the blood glucose of the human body. Referring first to FIG. 3, the user first drips a blood sample W into the reaction tank 30 of the electrochemical sensing test piece A. After the blood sample W is guided into the reaction tank 30 from the test sample port 31, the hemocyte of the blood sample W will be blocked and filtered through the porous filter layer 40, then the blood sample W containing only serum is guided to the chemical reaction zone 50 through the quantitative diversion layer 60. In such a case, the glucose in the blood sample W generates electrons via chemical reaction with the chemical reaction zone 50. The electrons will be accumulated in the reaction zone 22 of the electrode unit 20, and then the blood glucose tester 70 energizes the electrode unit 20 of the electrochemical sensing test piece A and provides a fixed voltage, thereby detecting the number of electrons accumulated in the reaction zone 22. The current is computed by the conversion formula embedded into the blood glucose tester 70, so the concentration of glucose in the blood sample W can be obtained.

Thus, the advantages of electrochemical sensing test piece A lie in that, whenever the blood sample W is dripped, the porous filter layer 40 is arranged such that the blood sample W of the chemical reaction zone 50 is treated by the same procedure to maintain the consistent measurement criterion.

Figure 5:
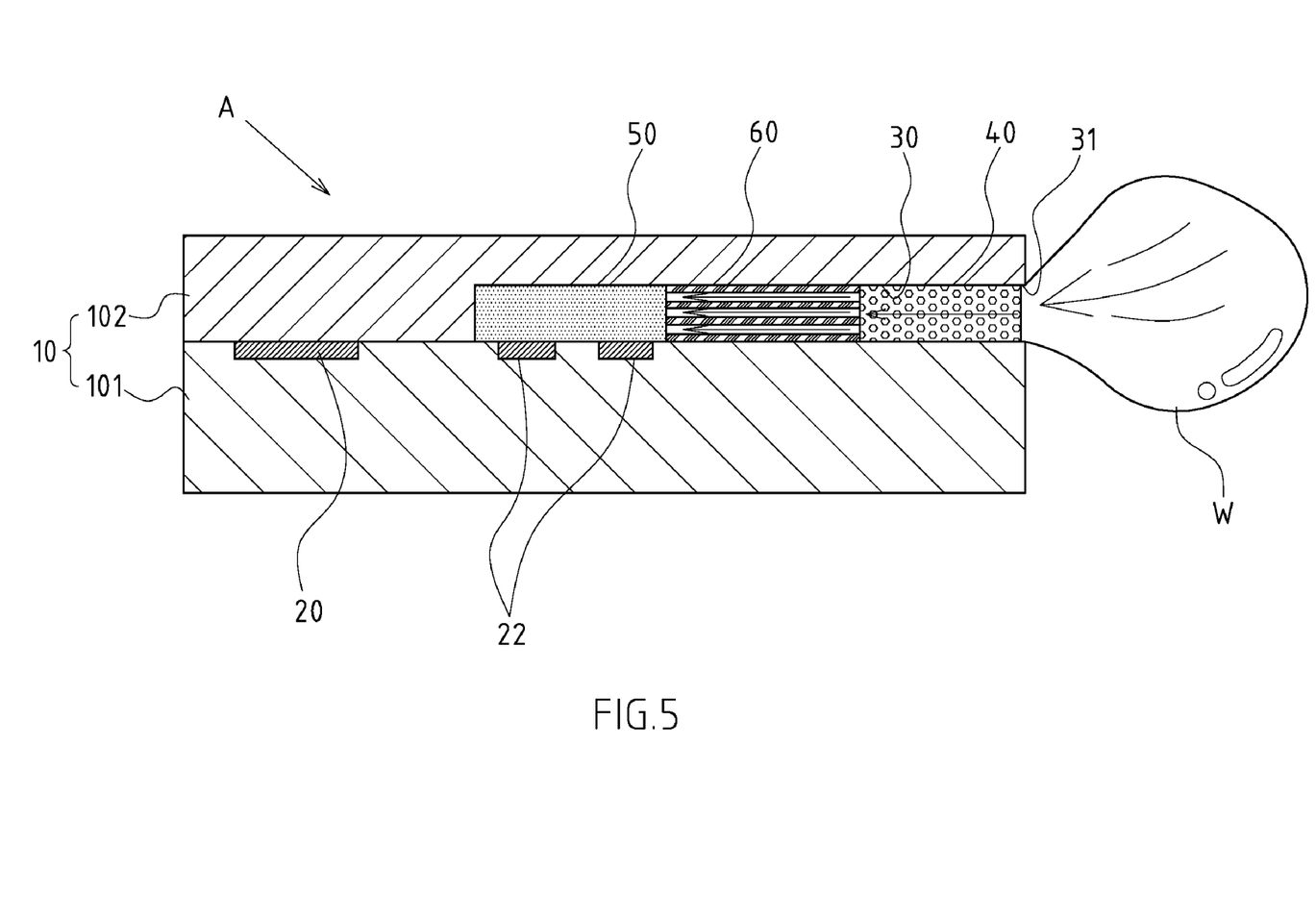
FIG. 5 shows a sectional view of the present invention that the porous filter layer, quantitative diversion layer and chemical reaction zone being arranged transversely.

The porous filter layer 40, quantitative diversion layer 60 and chemical reaction zone 50 are arranged transversely (shown in FIG. 5) and also superimposed vertically (shown in FIG. 3).

Figure 6:
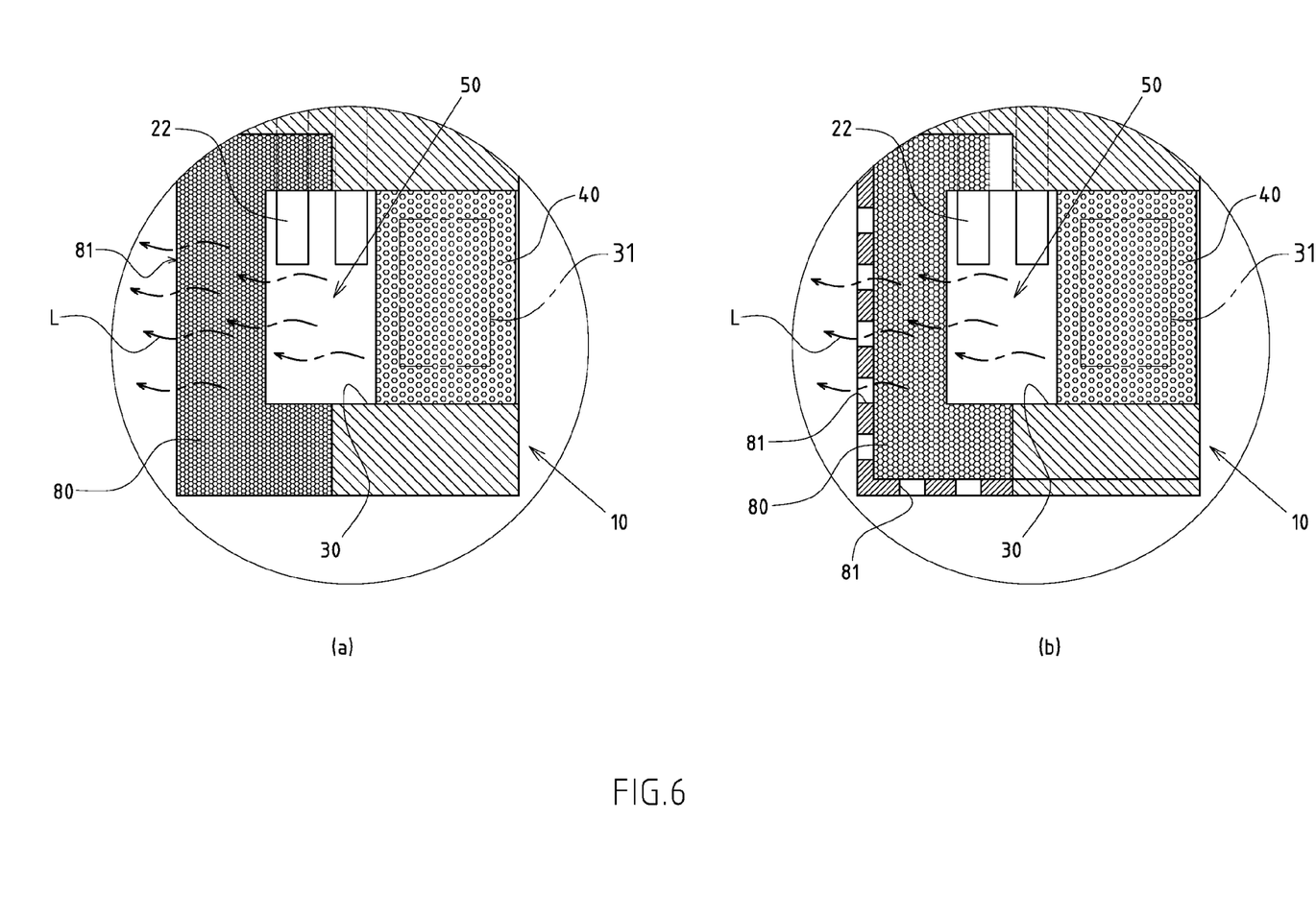
FIG. 6(a)-(b) show sectional view of the application of the present invention, showing a capillary tissue is arranged laterally on the chemical reaction zone.

Referring to FIG. 6(a), capillary tissue 80 is arranged on preset location of the chemical reaction zone 50 far away from the porous filter layer 40 (partially or fully arranged). The capillary tissue 80 is arranged laterally across the main body 10, so that the blood sample W entering into the chemical reaction zone 50 can be absorbed so as to prevent the blood sample W from being blocked at the porous filter layer 40. Referring also to FIG. 6(*b*), an air permeable portion 81 is arranged externally on the capillary tissue 80, so that the air can be leaked (shown by arrow L), and the blood sample W can be guided more smoothly. The air permeable portion 81 is formed by the capillary tissue 80 and external contact surface (shown by FIG. 6(*a*)), or by the porous structure (shown by FIG. 6(*b*)).

Figure 7:
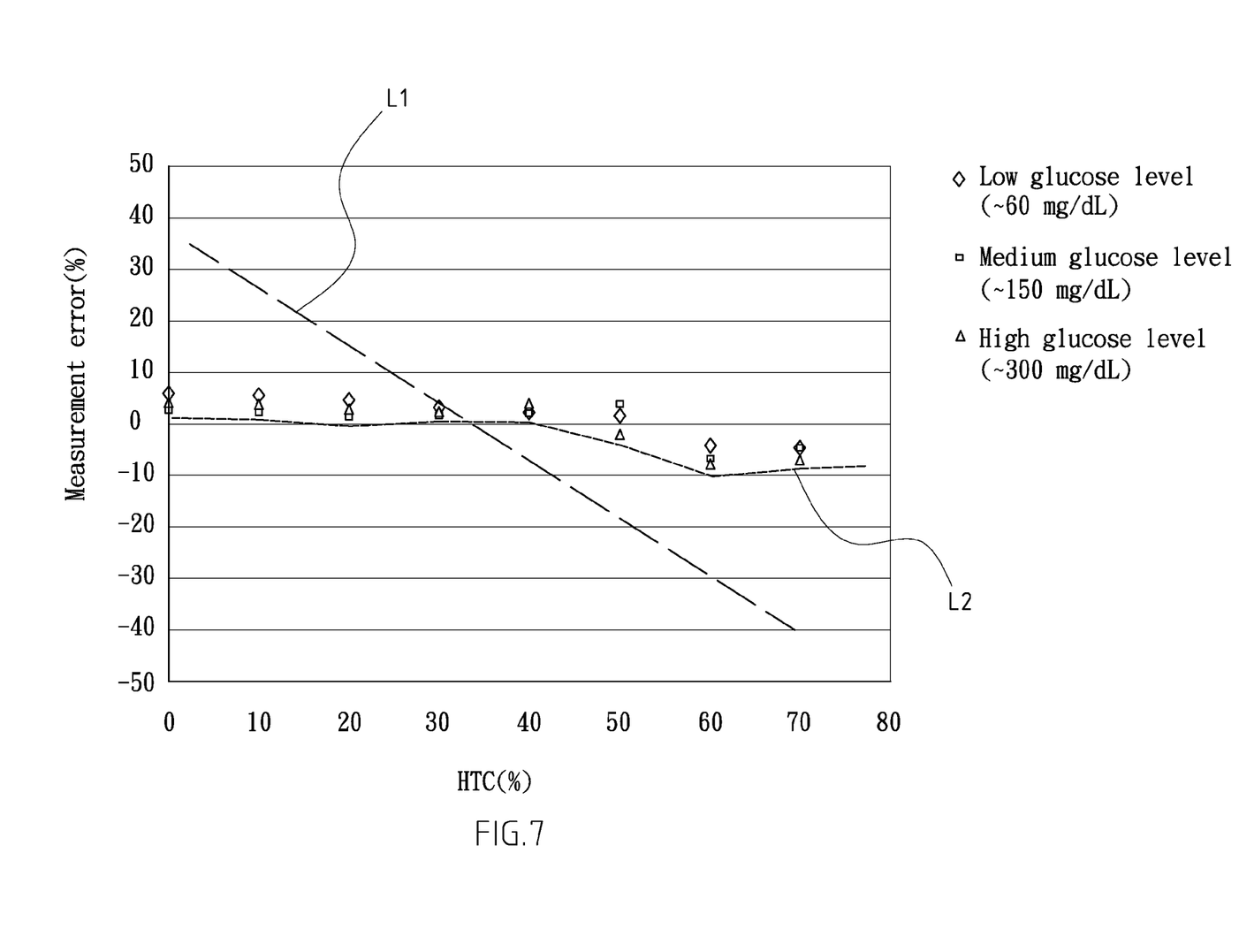
FIG. 7 shows a graph illustration, comparing measurement error between the electrochemical sensing test piece of the present invention and typical sensing test piece.

Referring to FIG. 7, there is a comparison view of the measurement error between the electrochemical sensing test piece A of the present invention and the typical sensing test piece, wherein curve L1 shows the measurement error of typical sensing test piece. The bigger or smaller the test sample's HCT, the bigger the measurement error is. As seen, with HCT at 0~70%, the measurement error of typical sensing test piece reaches approx. ±40%. Curve L2 shows the measurement error of the electrochemical sensing test piece A of the present invention, which is controlled within ±10% if HCT is 0~70%.

Figure 8:
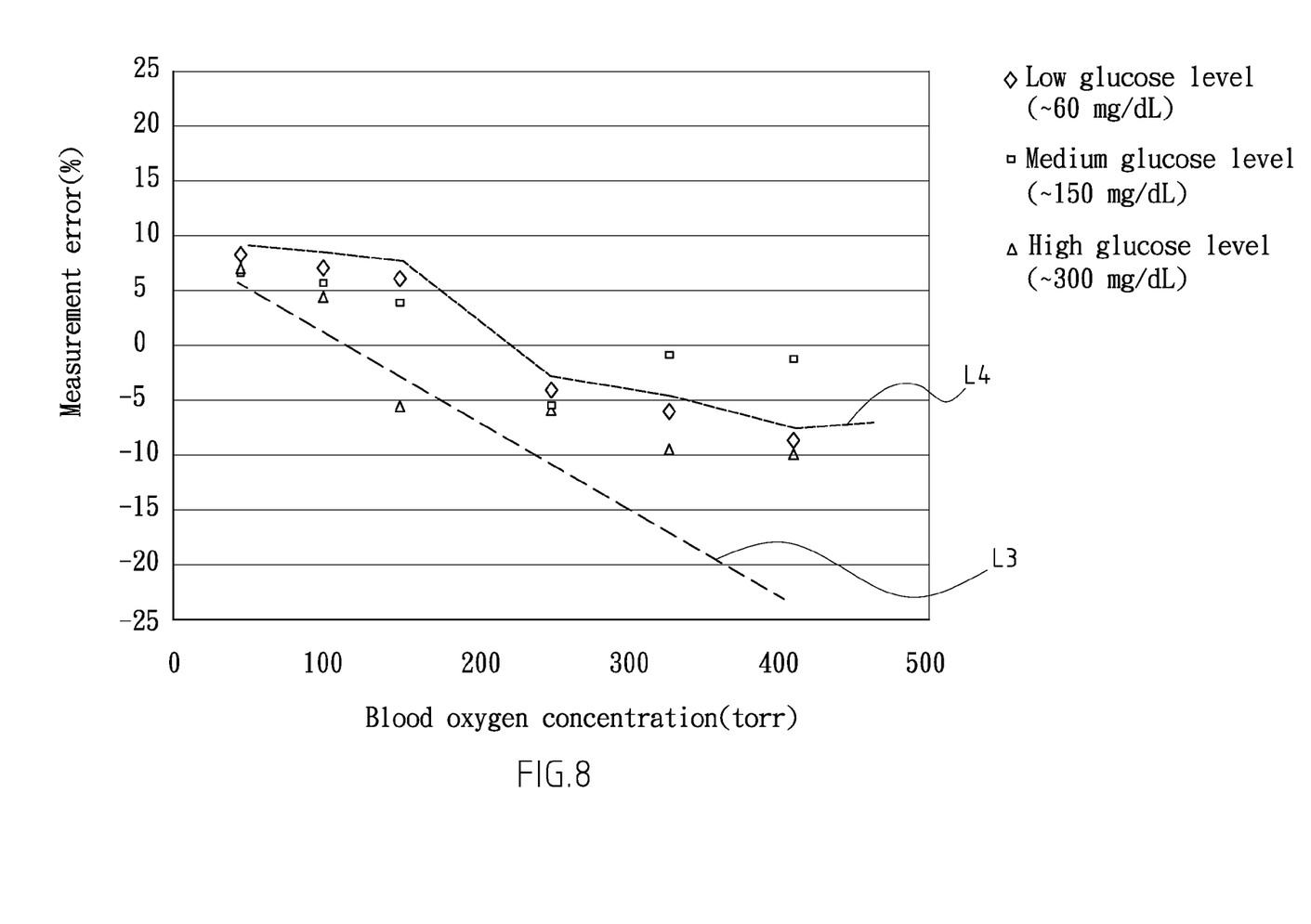
FIG. 8 shows a graph illustration, comparing measurement error between the electrochemical sensing test piece of the present invention (containing protein absorbent) and typical sensing test piece.

Referring also to FIG. 8, there is a comparison view of the measurement error between the electrochemical sensing test piece A of the present invention (removal of erythrocyte and heme) and typical sensing test piece (with Oxidase), wherein curve L3 shows the measurement error of typical sensing test piece. The bigger the torr of the test sample, the bigger the measurement error is. As seen, as the torr reaches 400, the measurement error of the typical sensing test piece is approx. ±25%. When the electrochemical sensing test piece A of the present invention contains protein absorbent, the error is indicated by curve L4, namely, the error is controlled within ±10% when the torr reaches 400.

Figure 9:
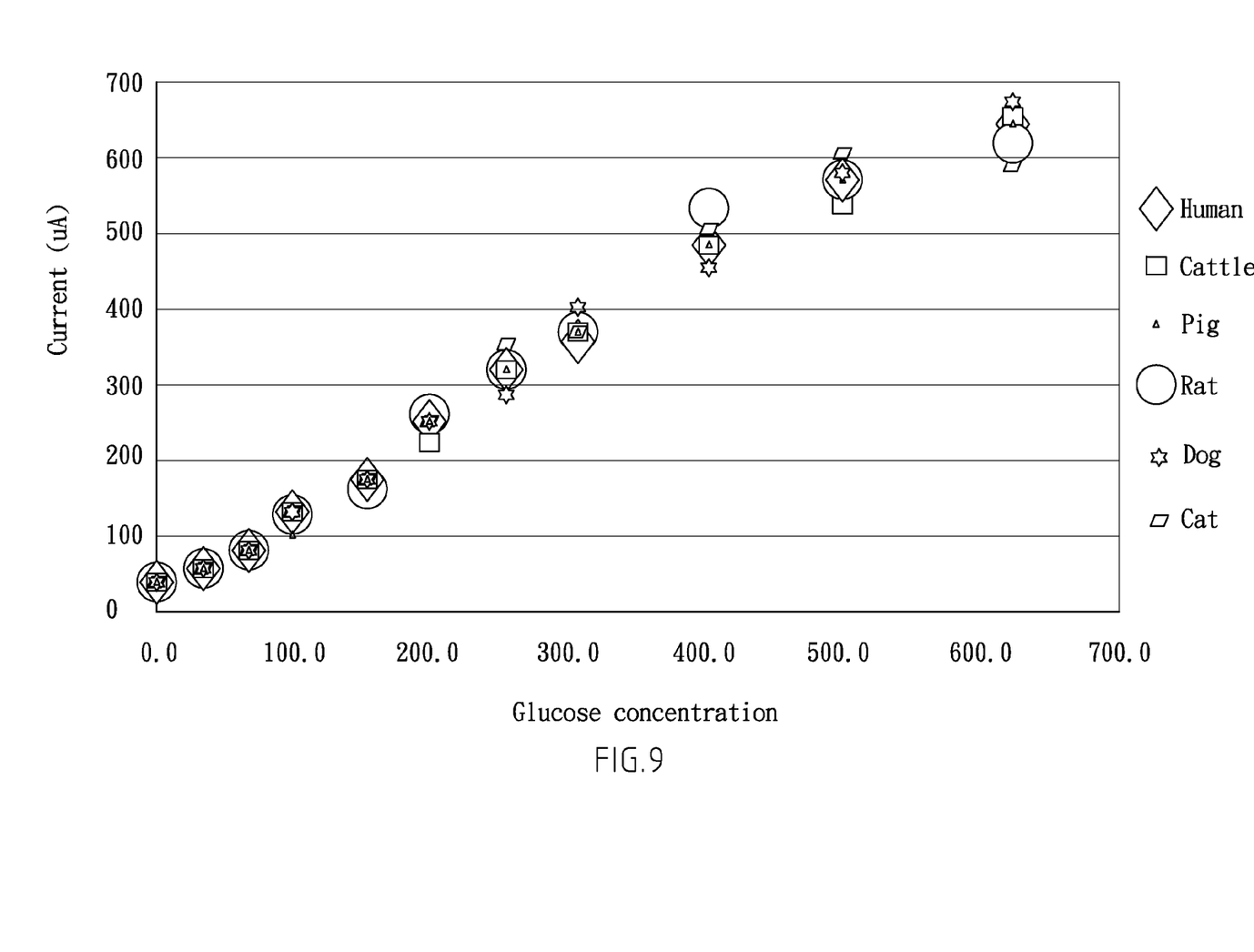
FIG. 9 shows a graph illustration, comparing measurements by the electrochemical sensing test piece of the present invention as applied to human beings and animals.

FIG. 9 is a comparison of the measurement states when the electrochemical sensing test piece A of the present invention, containing protein absorbent as applied to the human body and some animals. This aims to confirm that the measurement state and effect is consistent no matter the electrochemical sensing test piece A is applied to measure the blood sample of the human beings or animals. Thus, it is used in a wide range of applications.

We claim:

1. An electrochemcial sensing apparatus without hemocyte interference, the apparatus comprising:
   a main body containing an inserting end and a sensing end;
   an electrode unit assembled onto said main body, said electrode unit containing a detection zone and a reaction zone, said detection zone corresponding to said inserting end of said main body, said reaction zone corresponding to said sensing end of said main body;
   a reaction tank assembled onto said sensing end of said main body, said reaction tank having a test sample port;
   a porous filter layer positioned into said reaction tank, said porous filter layer being of a porous structure having apertures therethrough, each of said apertures having a diameter of less than 6 µm so as to separate hemocytes in a blood sample;
   a chemical reaction zone arranged between said porous filter layer and said reaction zone of said electrode unit; and
   a capillary tissue arranged on a preset location of said chemical reaction zone away from said porous filter layer.

2. The apparatus of claim 1, said porous filter layer being of a charcoal material.

3. The apparatus of claim 1, said reaction tank having a test sample port, said porous filter layer having one side extended to said test sample port.

4. The apparatus of claim 1, said main body being superimposed by an insulating substrate and a cover plate.

5. The apparatus of claim 1, further comprising:
   a quantitative diversion layer arranged between said porous filter layer and said chemical reaction zone.

6. The apparatus of claim 1, said porous filter layer containing a protein absorbent.

7. The apparatus of claim 1, said capillary tissue having an air permeable portion arranged externally thereof.

\* \* \* \* \*